(12) United States Patent
Jaafar et al.

(10) Patent No.: US 6,692,486 B2
(45) Date of Patent: Feb. 17, 2004

(54) APPARATUS AND METHOD FOR TREATMENT OF CEREBRAL ANEURYSMS, ARTERIAL-VASCULAR MALFORMATIONS AND ARTERIAL FISTULAS

(75) Inventors: Ali Jaafar, Eden Prairie, MN (US); Victor I. Chornenky, Minnetonka, MN (US)

(73) Assignee: Minnesota Medical Physics, LLC, Eden Prairie, MN (US)

( * ) Notice: Subject to any disclaimer, the term of this patent is extended or adjusted under 35 U.S.C. 154(b) by 0 days.

(21) Appl. No.: 09/849,324

(22) Filed: May 7, 2001

(65) Prior Publication Data

US 2002/0045848 A1 Apr. 18, 2002

Related U.S. Application Data

(60) Provisional application No. 60/202,541, filed on May 10, 2000.

(51) Int. Cl.[7] .............................................. A61B 18/18
(52) U.S. Cl. ................................ 606/7; 606/3; 606/15; 607/88; 607/89; 128/898
(58) Field of Search .................. 606/3, 7, 10, 13–21; 604/19–21, 22, 43, 508–510, 915–921; 600/101; 128/898

(56) References Cited

U.S. PATENT DOCUMENTS

| 5,092,841 | A | * | 3/1992 | Spears | 604/96 |
| 5,921,954 | A | * | 7/1999 | Mohr, Jr. et al. | 604/53 |
| 5,925,016 | A | * | 7/1999 | Chornenky et al. | 604/96 |
| 6,045,532 | A | * | 4/2000 | Eggers et al. | 604/144 |
| 6,428,531 | B1 | * | 8/2002 | Visuri et al. | 606/7 |
| 6,440,124 | B1 | * | 8/2002 | Esch et al. | 606/7 |
| 6,463,317 | B1 | * | 10/2002 | Kucharczyk et al. | 600/411 |

* cited by examiner

*Primary Examiner*—Lee Cohen
*Assistant Examiner*—Ahmed M Farah

(57) ABSTRACT

An apparatus and method for stabilization of aneurysm is disclosed. The apparatus comprises an ultraviolet radiation generator for generating UV radiation having a wavelength, strongly absorbed by the DNA and a catheter including means for delivering the ultraviolet radiation to the aneurysm. The distal end of the catheter is placed inside the aneurysm. Stabilization of the aneurysm is achieved by forming a mural arterial thrombus inside the aneurysm. To make irradiation possible, the blood is displaced from the aneurysm by a steady stream of UV radiation transparent fluid. The injury to the endothelium that triggers the thrombus formation is caused by UV radiation delivered to the aneurysm. In several days after intervention the thrombus becomes fully organized, leaving on the inside surface of the aneurysm a thick layer of fibrotic tissue that stabilizes the aneurysm.

6 Claims, 5 Drawing Sheets

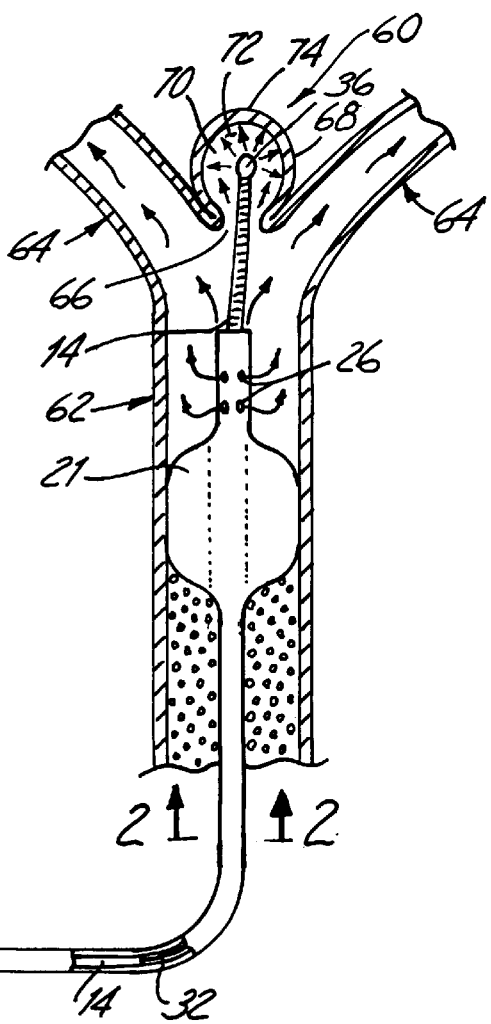
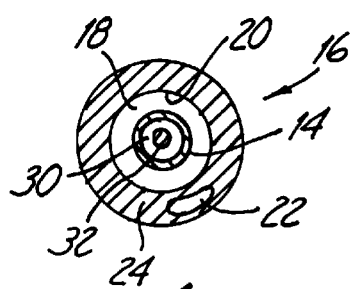
Fig. 2
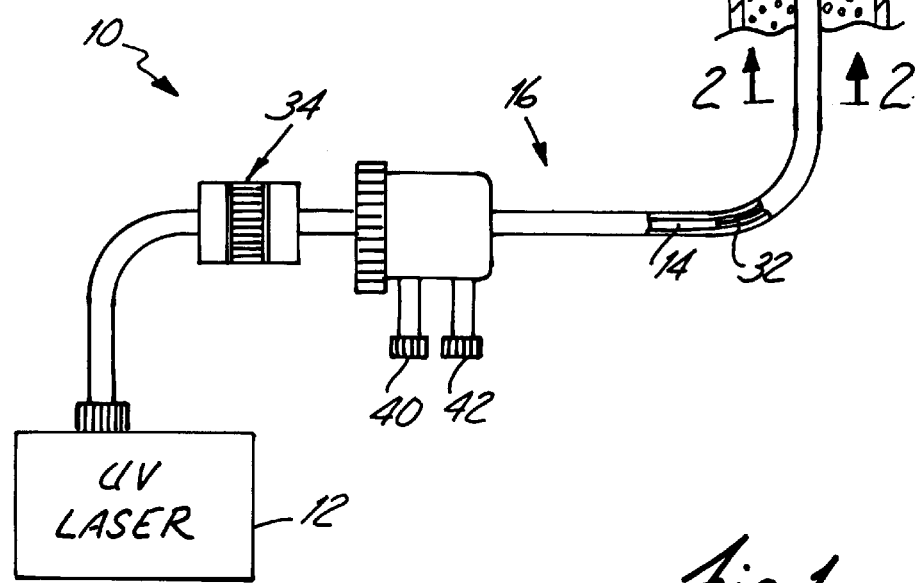
UV LASER
Fig. 1

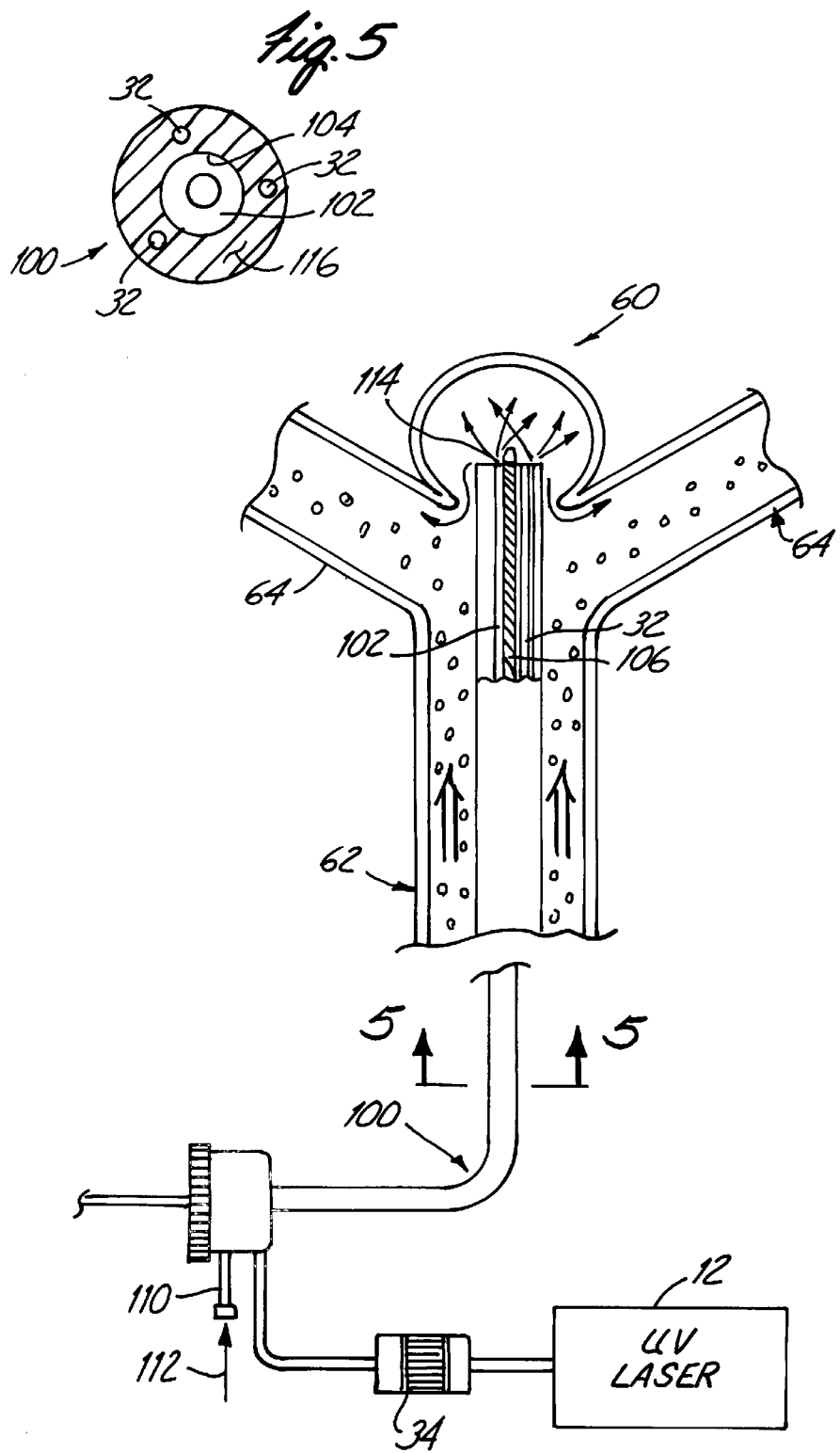

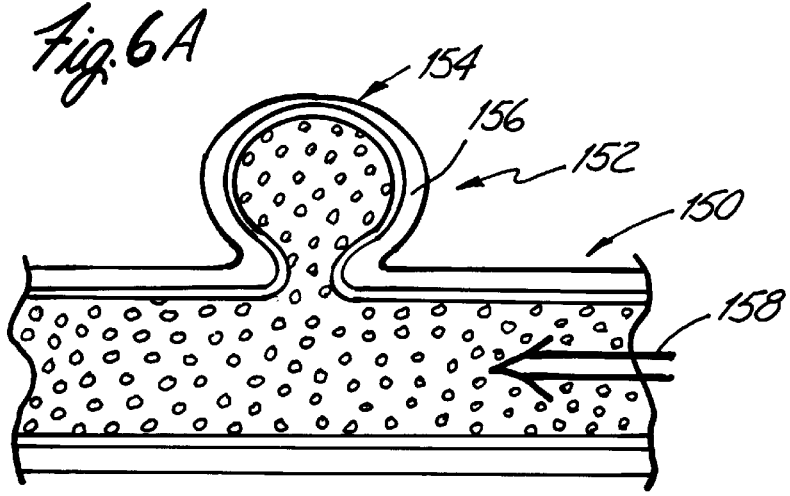
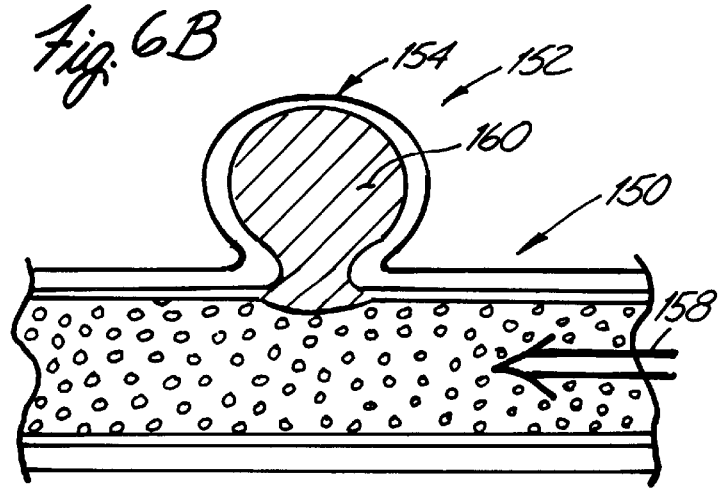
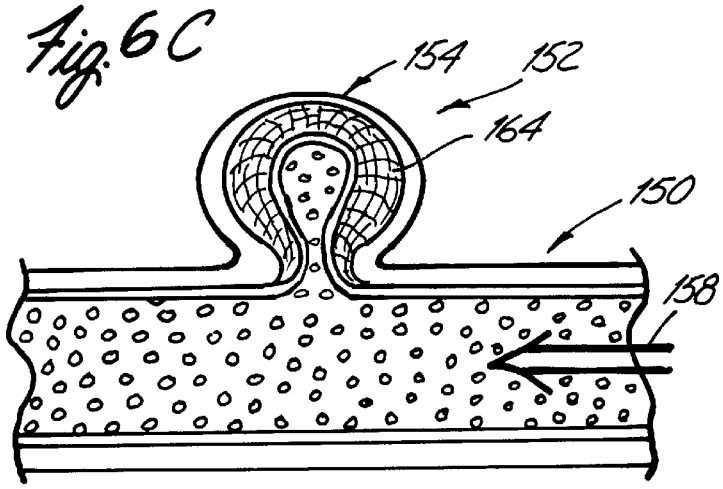

APPARATUS AND METHOD FOR TREATMENT OF CEREBRAL ANEURYSMS, ARTERIAL-VASCULAR MALFORMATIONS AND ARTERIAL FISTULAS

This application claims the benefit of provisional application Ser. No. 60/202,541 filed on May 10, 2000.

FIELD OF THE INVENTION

The present invention relates generally to apparatus and methods for the treatment of vascular disease and particularly to apparatus and method for treatment of cerebral aneurysms, arterial vascular malformations and arterial fistulas using lasers.

BACKGROUND INFORMATION

Cerebrovascular disease is the third leading cause of death in the United States, ranking behind only coronary artery disease and cancer. This disease can take several forms, including but not limited to cerebral aneurysm, arterial venous malformations (AVMs) and arterial fistulas (collectively referred to hereafter as "aneurysms.") One of the most important forms of this disease is the cerebral aneurysm, which manifest itself as a dilatation, or pouching of the arterial wall. As the disease progresses, the dilatation develops into a distended sac of thinned, stressed arterial tissue with a size of 5 to 10 mm in diameter. If not treated, an aneurysm continues to grow until it ruptures, causing a subarachnoid hemorrhage (that is, bleeding between the middle membrane covering of the brain and the brain itself), severe neurological complications, and, possibly, death.

The components of the arterial wall that are primarily responsible for its mechanical strength and elasticity are the structural proteins collagen and elastin. Collagen, which serves a protective function, is very extensible and breaks at a stress of about 500 megapascals. Collagen is the substance that gives the artery wall its high resistance to the hemodynamic forces created by the heart pumping the blood through the vessel. Elastin fibers, on the other hand, can stretch to about 250% of their original length and have about 20 times lower modulus of elasticity than collagen. These two proteins cooperate to provide vessels with sufficient strength and flexibility to withstand the continuous pounding and pressure of the blood as it flows through the vessel in response to the beat of the heart.

A fully developed cerebral aneurysm, however, consists almost entirely of collagen fibers, because the majority of the elastin fibers are fragmented by the distending forces of blood pulsating through the vessel in response to the rhythmic beat of the heart. This loss of elastin fibers is especially true for the top of aneurysm, where the tissue degradation is more advanced than in the base and the sidewalls of the aneurysm. Most ruptures consequently occur at the top, or dome, of the aneurysm. The aneurysm ruptures when its wall become too thin to withstand circumferential stresses imposed by the pressure differential between the arterial lumen and the subarachnoid space outside the artery.

Each year about 30,000 North Americans are diagnosed with a ruptured aneurysm and more than half of them die within the first thirty (30) days thereafter. Diagnosis and successful treatment of an aneurysm prior to its rupture is therefore critical to improving the survivability of a patient to this disease. The fundamental objective in the management of an aneurysm that has not ruptured is to stabilize it, thus avoiding further dilatation or growth. Aneurysm stabilization is currently accomplished by:

1) Conventional neurosurgical intervention, which cuts off the blood flow from the vessel to the aneurysm by ligating its neck with a metal clip;
2) Endovascular embolization with metallic or other solid mechanical objects causing thrombosis—clotting—inside the aneurysm; and
3) Thrombus generation within the aneurysm by heating the blood with a catheter having an insulated heating coil at its distal end.

An example of the endovascular approach is given in U.S. Pat. No. 5,354,295 entitled "An Endovascular Electrolytically Detachable Wire And Tip For The Formation Of Thrombus In Arteries, Veins, Aneurysms, Vascular Malformations And Arteriovenous Fistulas" issued on Oct. 11, 1994 to Guido Guglielmi at al. In this patent a method of treatment of aneurysms is described, in which an aneurysm is packed with detachable platinum wires, causing blood stagnation and blood clot formation inside the aneurysm. The clot prevents arterial blood from reaching the cavity of the aneurysm and continuing to apply pressure to the wall of the aneurysm and helps to stabilize the aneurysm.

In U.S. Pat. No. 5,919,187, issued on Jul. 6, 1999 to Guido Guglielmi, and entitled "Method And Apparatus For Endovascular Thermal Thrombosis And Thermal Cancer Treatment," a method and apparatus for endovascular thermal thrombosis is described. In this version of the endovascular approach to treatment, a thrombus is generated in an aneurysm, arteriovenous malformation (AVM) or fistula by heating the blood with a catheter having an insulated heating coil at its distal end.

The described methods are not applicable to aneurysms that do not have obviously defined necks (narrow openings between the artery and the aneurysm sac). Such aneurysms can't hold the wires or other emboli inside the cavity. Another shortcoming of the described methods is that the blood clot, formed by blood stagnation inside the cavity or its heating, is relatively weak. The fresh arterial blood, coming into the aneurysm can cause lysis (dissolution) of the clot inside the sac and create a chance that a piece of wire or a piece of clot can be displaced from the aneurysm into the blood stream and embolize distally.

A new treatment is needed that is free from these shortcomings and will improve the stabilization of aneurysms by improved methods and apparatus. The present invention provides an apparatus and method that stabilizes aneurysms of different shapes and produces a clot that is much more resistant to wash out by the blood flow.

SUMMARY OF THE INVENTION

The invention is an apparatus and method for forming a mural arterial thrombus, that is, a thrombus grown on and attached to the vascular wall inside a cerebral aneurysm, with emphasis on the formation of the arterial thrombus on the inner surface of the dome and the neck of the aneurysm.

In the present invention, formation of the desired arterial thrombus begins with an injury to the endothelium of the vascular wall of the aneurysm. This injury, which triggers the coagulation sequence within an aneurysm, is created by ultraviolet (UV) radiation delivered to the inner surface of the aneurysm by a micro catheter. The micro catheter comprises a steerable guide wire with an optical fiber in it. The proximal end of the optical fiber is coupled to a laser capable of producing (UV) radiation. The distal end of the guide wire, which emits UV radiation scattered in different directions, is placed inside the aneurysm. A dose of UV radiation, sufficient to cause complete necrosis of the endothelium and lead to the formation of the arterial thrombus, is delivered to the whole surface of the aneurysm.

Preferably, the blood is displaced from the aneurysm by a UV radiation transparent fluid, such as saline. Saline for this purpose may be delivered into the aneurysm from a pressurized saline bag or by a pump outside the patient via a plastic micro tube placed over the guide wire. In one implementation of the present invention a soft balloon, secured around the plastic micro tube, temporarily occludes the artery, thus ensuring better transparency inside the aneurysm. After delivery of the appropriate dose of UV radiation, the saline wash is terminated allowing blood to flow again into the aneurysm.

In another implementation of the invention an optical fiber (or multiple fibers) is placed inside the wall of the plastic micro tube delivering saline to the aneurysm. In this case a conventional guide wire is used for placing the tip of the micro catheter inside the aneurysm, and the blood flow in the feeding artery is not occluded even temporarily. The UV radiation is delivered to the aneurysm wall in the same manner as in the first implementation.

The foregoing method also may be used for the treatment of AVMs and arterial fistulas.

The foregoing objects of the invention will become apparent to those skilled in the art when the following detailed description of the invention is read in conjunction with the accompanying drawings and claims. Throughout the drawings, like numerals refer to similar or identical parts

BRIEF DESCRIPTION OF THE DRAWINGS

FIG. 1 illustrates an apparatus for treatment of cerebral aneurysms in accord with the present invention.

FIG. 2 is a cross-section taken along viewing plane 2—2 of FIG. 1.

FIG. 4 depicts another embodiment of an apparatus for treatment of cerebral aneurysms in accord with the present invention.

FIG. 5 is a cross sectional view of the embodiment shown in FIG. 4 taken along viewing plane 5—5.

FIGS. 6A, 6B, and 6C shows several stages of treatment of an aneurysm.

DESCRIPTION OF PREFERRED EMBODIMENT

Figure 3:
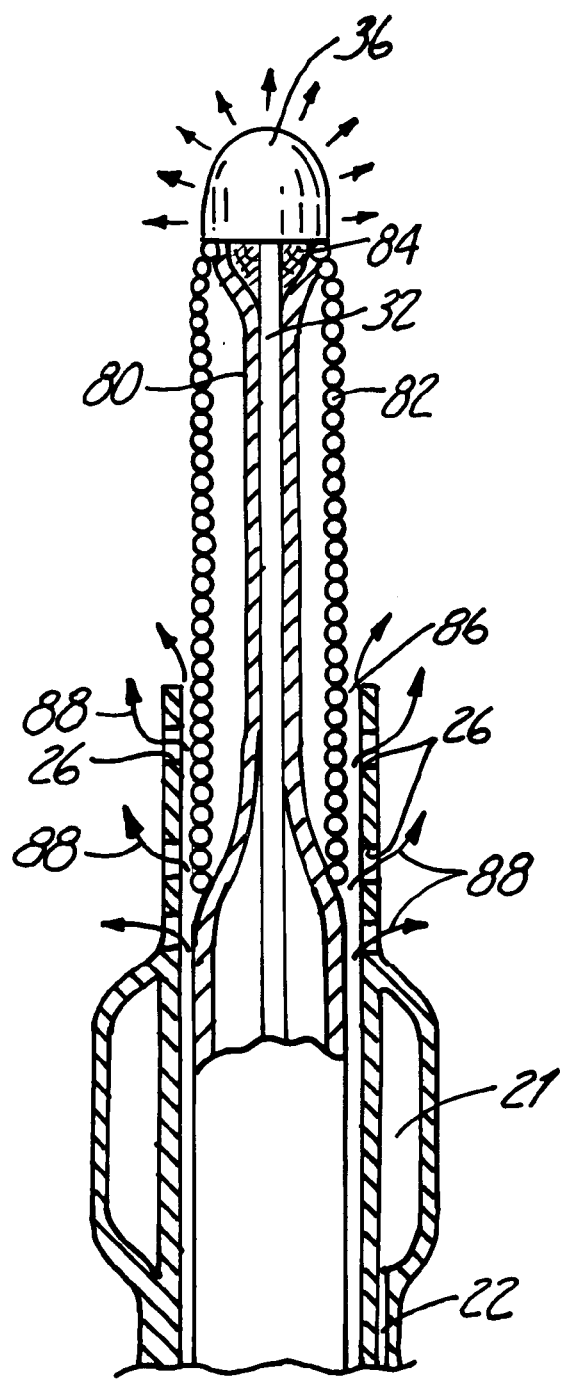
FIG. 3 presents a detailed view of the distal end of a catheter in accord with the present invention.

An apparatus 10 for treatment of an aneurysm and in accord with the present invention is schematically shown in FIGS. 1 and 2. Apparatus 10 comprises a laser 12, a steerable guide wire 14, and a catheter 16. Catheter 16 will be appropriately sized depending upon where in the patient's body a treatment will occur. For treatment of a cerebral aneurysm, which may require navigation through very small blood vessels in the brain, catheter 16 will be a microtube in the form of an elongated tube and may include a substantially centrally disposed tubular passage 18 defined by a wall 20 for receiving guide wire 14. Catheter 16 may, as shown in FIG. 1, also include an expandable balloon 21, which is used for occluding an artery during an interventional surgical procedure. Catheter 16 may also include a channel 22 disposed in the catheter wall 24 that is in fluid communication with balloon 21.

Guide wire 14 has a tubular configuration and thus defines a tubular passage 30 receiving an optical fiber 32. The rigid proximal end (not shown) of the guide wire 14 is connectable to a fiber optic connector 34, which couples the output of the UV laser 12 to the fiber 32. Fiber 32 is secured substantially coaxially at the center of guide wire 14. The optical fiber 32 terminates in an optical tip 36 disposed at the distal end thereof.

The proximal end of the catheter 16 has two hermetic fluid ports 40 and 42 for receiving a fluid from external fluid sources, typically saline. Port 40 communicates with balloon 21 through the channel 22 in the wall 24 of catheter 16 and serves for inflation of the balloon through the flow of saline from an external source (not shown) through the port 40, into the channel 22 and from there into balloon 21. The space between the external surface of guide wire 14 and the wall 20 of catheter passage 18 define a second channel for fluid flow. This second channel communicates with port 42, which may also be fluidly connected to an external fluid source such as saline to provide a clear fluid distally of balloon 21 through the holes 26.

Referring to FIG. 1, it will be observed that an aneurysm 60 has formed at the branch of a parent artery 62 into a pair of daughter arteries 64. The aneurysm 60 includes a neck 66, a sac 68 defining a cavity 70 lined with endothelial cells, which form the inner wall or surface 72 of an artery (and hence the sac), and a dome 74.

The catheter is placed in the blood vessel over the guide wire 14 (0.009" to 0.014" in diameter). The guide wire 14 has a hollow tubular configuration and according to the present invention is made of a metallic material, though it will be understood that other materials now known or hereafter developed could also find use as a guide wire.

To provide the desired flexibility, fiber 32 has diameter of about fifty (50) micrometers or less and preferably in a range of about twenty-five (25) to about fifty (50) micrometers. Fiber 32 is preferably a multimode fiber made of fused silica adapted for the efficient transmission of UV radiation. The optical tip 36 is transparent (or translucent) for the UV radiation and is made, for example, of sapphire or fused silica. The surface of the optical tip 36 is mated to the fiber 32 and configured so as to diffuse UV light in the forward and side directions to better illuminate the inner surface 72 of the aneurysm 60. The UV radiation propagates in the optical fiber 32 from its proximal end to the distal end which is terminated with the optical tip 36. The optical tip 36 scatters the radiation in different directions to the aneurysm's wall 72. The optical tip 36 is desirably positioned inside the aneurysm 60 at different distances from the aneurysm wall 72. During irradiation of the dome 74 the distance between the optical tip 36 and the inner surface 7 is short, ranging from about one down to zero mm while during irradiation of the neck 66 the optical tip 36 is placed therewithin.

The laser can be pulsed or continues wave (CW), with the preferred form being a CW Ion Argon laser generating UV radiation with wavelength 257 nm, which is strongly absorbed by the DNA of the endothelial cells. Preferably, the energy source, regardless of its particular embodiment, should generate ultraviolet radiation in the range of about 240 to about 280 nanometers, corresponding to maximum UV absorption in DNA.

FIG. 3 represents enlarged view of the distal end of the catheter. Guide wire 14 is illustrated as a low profile metal tube 80 with fiber 32 disposed thereinside with a spiral, thin wire 82 around it, brazed at both ends to the metal tube 80.

The optical tip 36 can be secured to the end of the tube 80 and fiber 32 with an epoxy or other glue 84. Wash fluid flow through the holes 26 and out of the open end 86 of the catheter 16 is illustrated by arrows 88.

FIGS. 4 and 5 show another implementation of the present invention. In the embodiment shown in the Figure, a catheter 100 is used to deliver the necrotizing UV radiation to the aneurysm 60. Catheter 100 does not include an expandable balloon to occlude the artery 62 and thus can have a simpler construction than the catheter shown in FIGS. 1–3. Catheter 100 comprises a single elongate tubular member including a central passage 102 defined by an inner wall 104. Passage 102 receives a guide wire 106. Because there is no need to inflate a balloon, there is no need for a separate port and interwall fluid channel such as channel 22 as shown in FIG. 2. Thus, catheter 100 includes a single hermetic fluid port 110 that receives a wash fluid such as saline from an external source as indicated by arrow 112. Port 110 is in fluid communication with passage 102, thus providing a flow path from the external fluid source through the port 110, through the passage 102 and out of the open end 114 of the distal end of the catheter 100.

Catheter 100 further includes one or more optical fibers 32 disposed within the catheter wall 116. Each fiber will include an optical tip 36 at its distal end attached in any known manner. The UV radiation will be delivered to the inner surface 72 of the aneurysm by the tips 36, each of which will radiate in a substantially semispherical direction in the same manner as the embodiment shown in FIG. 1. UV radiation will be delivered to the fibers 32 by laser 12 through the optical coupler 34.

A method of treatment of cerebral aneurysms comprises the steps of: a) inserting a fiber optic guide wire into an artery feeding an aneurysm, with the distal optical tip of the guide wire being placed inside the aneurysm; b) placing a balloon over the wire proximally to the optical tip of the guide wire; c) occluding the artery by inflating the balloon; d) clearing the optical field inside the artery and the aneurysm by delivering steady flow of fluid transparent or substantially transparent to UV radiation; e) activating a UV laser and delivering UV energy on the inside surface of the aneurysm in quantity sufficient for killing 99.9% or more of the endothelial cells on the irradiated surface of the aneurysm.

FIGS. 6A, 6B, and 6C illustrate generally the treatment of an aneurysm. FIG. 6B shows an artery 150 with an aneurysm 152. The aneurysm dome 154 reveals a thinner vessel wall 156 as a result of the distention of the vessel 150 at that location. Blood flow is indicated generally by arrow 158.

FIG. 6B illustrates the aneurysm following treatment with the present invention. It will be observed that a necrotized layer 160 of endothelial cells has been formed following treatment with UV radiation on the inside surface of the aneurysm.

FIG. 6C illustrates the aneurysm 152 after the formation of a "real arterial thrombus" 164. At the dome the thickness of the aneurysm's wall is the lowest and the probability of rupture is the highest (about 90% of all cerebral aneurysms are ruptured at the dome). Narrowing the neck of the aneurysm causes a decrease in the blood pressure within the aneurysm sac and thus assists in its stabilization. A "real arterial thrombus" significantly differs from a blood clot, as that term is usually used in the described methods of stabilization of aneurysms. The underlying core of the arterial thrombus consists of fibrin and aggregated platelets, which strongly adhere to each other and to the arterial wall. The color of the core is white, so an arterial thrombus is sometimes referred to as a "white thrombus". The margin or exterior layer of the arterial thrombus consists of coagulated blood and is red. Arterial thrombi form at the site of an injury to the endothelium, which exposes the highly thrombogenic connective tissue underlying the endothelial layer to the blood flow. This connective tissue, primarily collagen, causes activation of platelets, leading to the formation of a thrombus.

Necrotic endothelial cells are not able to produce tissue plasmogen activator t-PA, a major function of which is preventing thrombus formation on the vessel walls, and cannot stay attached to the vessel wall surface. As they are flaked off and carried away by the blood flow, the highly thrombogenic underlying layer consisting of collagen is exposed. Platelets from blood, activated at the endothelium-denuded surface of the aneurysm, start aggregation and the whole sequence of arterial thrombus formation on the irradiated surface of the aneurysm is launched. In several days after intervention the thrombus, contracted in volume and ingrown by capillaries and fibroblasts, becomes organized. The fully organized thrombus on the inside surface of the aneurysm leaves a thick layer of fibrotic tissue, covered with a newly restored endothelial layer, thereby stabilizing the aneurysm against rupture and further thrombosis.

The energy fluence, required for causing necrosis of the endothelial cells, falls in the range of several units to several hundreds of $mJ/cm2$, that is, within a range of about 5 to about 1000 $mJ/cm2$. The time required for achieving full necrosis of endothelial cells with a milliwatt UV laser, falls in the range of about 10 seconds to several minutes. It will be understood that the time period over which irradiating of the aneurysm with UV energy occurs is inversely dependent upon the applied energy. As the power of the applied radiation decreases, the duration of time over which the energy must be applied to cause the desired cell death increases and vice versa. An Argon ion laser, generating UV radiation with wavelength 257 nanometers or a Nd-YAG laser generating radiation with a wavelength 256 nanometers (the fourth harmonic of the infrared wavelength 1.06 microns) are just two examples of UV radiation sources that can be used in accord with the present invention.

Without functioning endothelial cells the aneurysm's inner wall becomes highly thrombogenic, triggering formation of thrombus on it and coagulation of the blood in the sac of the aneurysm. After organization of the thrombus the inner wall of the aneurysm will be covered with a thick layer (several hundred microns) of a collagen rich fibrous tissue. For a normal artery the thickening of its wall is a negative event. It results in a loss of patency and flexibility of the vessel. But for an aneurysm the thickening of the wall decreases actual tensile stresses in it and arrests the growth of the aneurysm. It follows from a well-known fact that circumferential stress, responsible for the aneurysm rupture, is inversely proportional to the aneurysm wall thickness:

$$S=PR/2h$$

where
S=Circumferential Stress;
P=Blood Pressure;
R=Radius of the Aneurysm; and
h=Thickness of the Aneurysm Wall.

A several time increase in wall thickness causes a several time drop in the stresses. The formula is taken from "The Physics of Cerebrovascular Disease" by George J. Hademenos and Tarik F. Massoud, Springer—Verlag, 1998, ISBN 1-56396-558-5.

The critical thickness of a saccular aneurysm, at which a rupture occurs, is around 40–50 microns. The thickness of a fibrous layer after full organization of thrombus reaches several hundred microns, thus warranting stabilization of the aneurysm by treatment with UV radiation.

Figure 7:
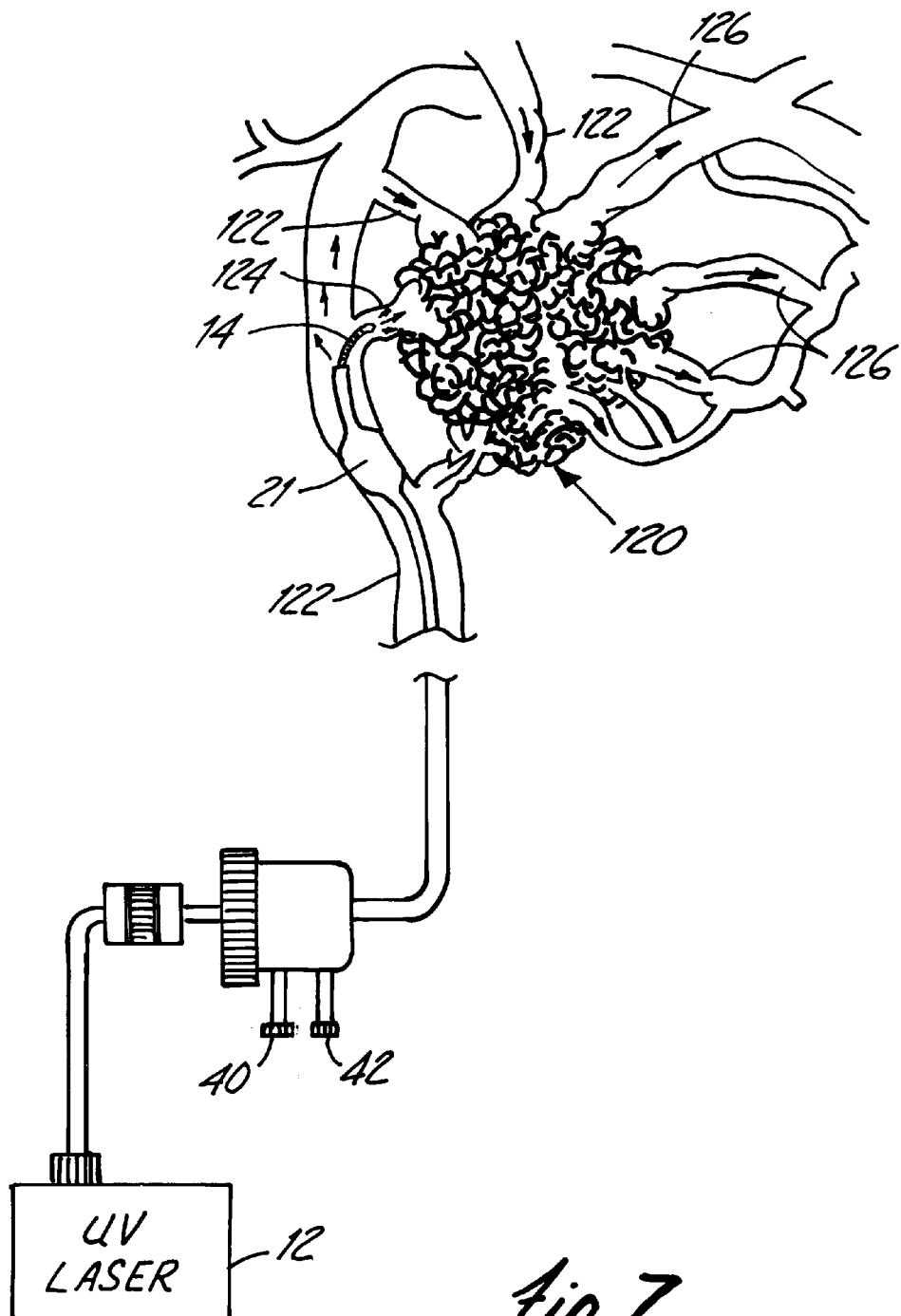
FIG. 7 shows the treatment of arterial venous malformations using an apparatus in accord with the present invention.

FIG. 7 schematically illustrates treatment of an arterial venous malformation (AVM) 120 in accord with the present invention. AVMs are massive blood formations wherein one or more feeding arteries provide blood to the mass, which is then drained by one or more draining arteries without the blood ever being supplied to the tissue, typically cerebral tissue. The formation of the AVM, then, results in starvation of the surrounding tissues because of the diversion of the fresh arterial blood from the tissue by the AVM. As shown in the figure, guide wire 14 with an optical fiber 32 inside is advanced through a feeding artery 122 to AVM 120. The optical tip 36 of the fiber 32 is placed into a shunting arteriole 124 of the AVM 120. The balloon 21 inflates and occludes the artery 122. Saline flow distally to the balloon 21 clears the feeder 122 and proximal part of AVM 120 from blood. The UV laser 12 is turned on and the feeder's wall and adjacent vessels of the AVM are irradiated by UV radiation emitted by the optical tip 36. This procedure is repeated with all feeding arteries of the AVM. After blood flow is restored, arterial thrombi are formed in the AVM and adjacent feeders. The thrombus after organization causes stenosis or closing of the feeders, significantly decreasing blood flow through the AVM and out through the draining vessels 126

It will be understood that the present invention can also be used to treat arterial fistulas in the same manner as previously described with reference to aneurysms and AVMs.

It will be obvious to those skilled in the art that many modifications may be made within the scope of the present invention without departing from the spirit of thereof, and the invention includes all such modifications. For example, it will be understood that other sources of ultraviolet radiation now available or hereafter developed could provide the necessary ultraviolet radiation and that the use of a laser is not required by the present invention, though with current technology it is preferred.

What is claimed is:

1. A method of treatment of an aneurysm, comprising the steps:

inserting a fiber optic guide wire having an optical tip into the artery feeding the aneurysm, the distal tip of the guide wire being placed inside the aneurysm;

clearing the optical field inside the artery and the aneurysm by delivering a wash fluid transparent to UV radiation to displace the blood;

activating a UV laser and delivering UV radiation through the guidewire on the whole inside surface of the aneurysm in quantity sufficient for killing 99.9% or more of the endothelial cells on the irradiated surface of the aneurysm such that a mural thrombus is formed and the aneurysm is strengthened against rupture.

2. The method of claim 1 and further comprising:

placing a catheter with an occlusive balloon just proximally to the optical tip of the guide wire; and occluding the artery by the balloon.

3. The method of claim 1 wherein the wash fluid is saline.

4. A method of treatment of aneurysms comprising the steps:

inserting a fiber optic guide wire including an optical tip artery feeding an aneurysm, the distal tip into the of the guide wire being placed in sufficient proximity to the inner wall of the aneurysm to deliver radiation thereto;

placing a catheter with an occlusive balloon and micro tube over the wire, the distal end of the tube disposed just proximally to the optical tip of the guide wire;

occluding the artery by the balloon;

clearing the optical field inside the artery and the aneurysm by delivering steady flow of saline; and delivering radiation through the guide wire to the inside surface of the aneurysm so as to cause the death of a sufficient number of the endothelial cells on the irradiated surface of the aneurysm such that the aneurysm forms a mural thrombus and thereby strengthens the aneurysm against rupture.

5. The method of claim 4 wherein the radiation is UV radiation generated by a UV laser.

6. A method of treatment of cerebral aneurysms and AVMs, comprising the steps:

inserting a guide wire including a distal tip into the artery feeding an aneurysm or AVM, the distal tip of the guide wire being placed inside the aneurysm or AVM;

placing a catheter over the wire, wherein the distal end of the catheter lies proximally to the tip of the guide wire;

clearing the optical field inside the artery and the aneurysm or AVM by delivering a steady flow of saline; and activating a UV laser and delivering UV radiation through the guide wire on the inside surface of the aneurysm or AVM in quantity sufficient for killing 99.9% or more of the endothelial cells on the irradiated surface of the aneurysm.

* * * * *